(12) United States Patent
Frenette et al.

(10) Patent No.: US 11,920,159 B2
(45) Date of Patent: Mar. 5, 2024

(54) METHODS FOR EXPANDING HEMATOPOIETIC STEM CELLS USING REVITALIZED MESENCHYMAL STEM CELLS

(71) Applicant: Albert Einstein College of Medicine, Bronx, NY (US)

(72) Inventors: Paul S. Frenette, New York, NY (US); Fumio Nakahara, Bronx, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 879 days.

(21) Appl. No.: 16/620,839

(22) PCT Filed: Jun. 7, 2018

(86) PCT No.: PCT/US2018/036408
§ 371 (c)(1),
(2) Date: Dec. 9, 2019

(87) PCT Pub. No.: WO2018/226926
PCT Pub. Date: Dec. 13, 2018

(65) Prior Publication Data
US 2020/0140823 A1 May 7, 2020

Related U.S. Application Data

(60) Provisional application No. 62/517,271, filed on Jun. 9, 2017.

(51) Int. Cl.
*C12N 5/0775* (2010.01)
*A61K 35/28* (2015.01)
*C12N 15/86* (2006.01)

(52) U.S. Cl.
CPC ............ *C12N 5/0663* (2013.01); *A61K 35/28* (2013.01); *C12N 15/86* (2013.01); *C12N 2506/11* (2013.01); *C12N 2506/30* (2013.01); *C12N 2740/15043* (2013.01)

(58) Field of Classification Search
None
See application file for complete search history.

(56) References Cited

U.S. PATENT DOCUMENTS

2007/0077652 A1 4/2007 Peled et al.
2016/0220699 A1* 8/2016 O'Heeron .......... A61K 48/0058

FOREIGN PATENT DOCUMENTS

WO 2012/054896 A1 4/2012
WO 2013/130769 A1 9/2013

OTHER PUBLICATIONS

Abm, Abmgood.com "OSTF1 Lentiviral"; accessed Dec. 2, 2022 (Year: 2022).*
Park et al. Engineering mesenchymal stem cells for regenerative medicine and drug delivery, Methods 84 (2015) 3-16) (Year: 2015).*
Woods et al. Dynamic Changes of the Bone Marrow Niche: Mesenchymal Stromal Cells and Their Progeny During Aging and Leukemia Front. Cell Dev. Biol. 9:714716. (Year: 2021).*
Nakahara et al. Engineering a haematopoietic stem cell niche by revitalizing mesenchymal stromal cells Nature Cell Biology | vol. 560 21 | May 2019 | 560-567 (Year: 2019).*
Balachandran, S., et al., "Far-Associated Death Domain-Containing Protein-Mediated Antiviral Innate Immune Signaling Involves the Regulation of Irf7," J. Immunol. 178:2429-2439 (2007).
Brenner, A. K., et al., "Mesenchymal Stem Cells Support Survival and Proliferation of Primary Human Acute Myeloid Leukemia Cells through Heterogeneous Molecular Mechanisms," Frontiers in Immunology 8:106 (2017).
Sriburi, R., et al., "XBP1: A Link Between the Unfolded Protein Response, Lipid Biosynthesis, and Biogenesis of the Endoplasmic Reticulum," J. Cell Biol. 167(1):35-41 (2004).
United States Patent and Trademark Office, International Search Report and Written Opinion dated Sep. 24, 2018 for International Application No. PCT/US2018/036408, 16 pages.

* cited by examiner

*Primary Examiner* — Laura Schuberg
*Assistant Examiner* — Alexandra F Connors
(74) *Attorney, Agent, or Firm* — Perkins Coie LLP

(57) ABSTRACT

A method for revitalizing mesenchymal stem cells (MSC) maintained in culture by transducing the MSC with vectors encoding a specific gene combination, as well as methods of use of MSC so revitalized in co-culturing hematopoietic stem cells.

3 Claims, 13 Drawing Sheets f control 5 genes (KOXII)

METHODS FOR EXPANDING HEMATOPOIETIC STEM CELLS USING REVITALIZED MESENCHYMAL STEM CELLS

CROSS-REFERENCE TO RELATED APPLICATIONS

This application is a 371 National Phase entry of International Application No. PCT/US2018/036408, which claims the benefit of U.S. Provisional Application No. 62/517,271, filed Jun. 9, 2017, the contents of which are hereby incorporated by reference.

STATEMENT OF GOVERNMENT SUPPORT

This invention was made with government support under grant numbers HL116340 and DK056638 awarded by the National Institutes of Health. The government has certain rights in the invention.

BACKGROUND OF THE INVENTION

Hematopoietic stem cells (HSCs) reside in bone marrow niche where they are maintained to replenish all blood cell lineages throughout life. Although HSCs have tremendous clinical utility by their ability to reconstitute the hematopoietic system by transplantation, their benefit remains limited due to lack of matched donors. Cord blood-derived cells have emerged as a promising alternative but the limited number of HSCs prevents transplantation in many adults. The ability to expand HSCs ex vivo would therefore be of significant clinical impact, but thus far most culture systems favor expansion of committed progenitors rather than stem cells. The interactions between the niche constituents and HSCs ensure hematopoietic homeostasis by regulating HSC self-renewal, differentiation, and migration. The bulk of the key factors recognized for HSC maintenance are synthesized by niche cells associated with the vasculature that have mesenchymal stem cell (MSC) capacity. However, upon culture in vitro these niche cells rapidly lose expression of the niche factors.

The present invention addresses the need for revitalizing cultured MSCs to boost their synthesis of niche factors and their ability to maintain healthy HSCs in in vitro conditions.

SUMMARY OF THE INVENTION

An isolated population of artificially modified mesenchymal stem cells (MSC) maintained in culture comprising MSC transduced with one or more vector(s), the vector(s) encoding the following genes: Klf7 (Kruppel-like factor 7), Ostf1 (osteoclast stimulating factor 1), Xbp1 (X-box binding protein 1), Irf3 (interferon regulatory factor 1), and Irf7 (interferon regulatory factor 7) under binding conditions permitting expression of genes.

A method is provided for revitalizing a mesenchymal stem cell (MSC) maintained in culture comprising transducing the MSC with one or more lentiviral vector(s), the lentiviral vector(s) encoding the following genes: Ostf1, Xbp1, Irf3, and Irf7 under conditions permitting expression of the genes, so as to revitalize the MSC.

Also provided is a kit comprising
one or more lentiviral vector(s), the lentiviral vector(s) encoding the following genes: Klf7 Ostf1, Xbp1, Irf3, and Irf7;
one or more reagents for culturing MSCs in vitro; and
instructions for using the lentiviral vector(s) to revitalize cultured MSCs.

Also provided is a method for co-culturing hematopoietic stem cells (HSC) and mesenchymal stem cells (MSC) comprising providing a culture of MSC pretreated with one or more lentiviral vector(s), the lentiviral vector(s) encoding the following genes: Ostf1, Xbp1, Irf3, and Irf7 under conditions permitting expression of the genes, and subsequently adding an amount of HSC to the MSC in culture, so as to co-culture the HSC and MSC.

Also provided is a method of treating a patient having a damaged or impaired bone marrow, comprising administering to the patient an amount of mesenchymal stem cells (MSC) previously maintained in culture and which have been transduced with one or more lentiviral vector(s), the lentiviral vector(s) encoding the following genes: Ostf1, Xbp1, Irf3, and Irf7 under conditions permitting expression of the genes.

Also provided is a method of preparing a patient for a bone marrow transplant, comprising administering to the patient an amount of mesenchymal stem cells (MSC) previously maintained in culture and which have been transduced with one or more lentiviral vector(s), the lentiviral vector(s) encoding the following genes: Klf7, Ostf1, Xbp1, Irf3, and Irf7 under conditions permitting expression of the genes in an amount effective to prepare a patient for a bone marrow transplant.

Also provided is a method for maintaining a leukemic stem cell (LSC) in culture comprising co-culturing the LSC with MSC transduced with one or more lentiviral vector(s), the lentiviral vector(s) encoding the following genes: Ostf1, Xbp1, Irf3, and Irf7 under conditions permitting expression of the genes, so as to revitalize the MSC.

Also provided is an isolated population of leukemic stem cells (LSC) maintained in culture with a plurality of MSC transduced with one or more lentiviral vector(s), the lentiviral vector(s) encoding the following genes: Klf7, Ostf1, Xbp1, Irf3, and Irf7 under conditions permitting expression of the genes.

Additional objects of the invention will be apparent from the description which follows.

DETAILED DESCRIPTION OF THE INVENTION

Figures 1A, 1B, 1C:
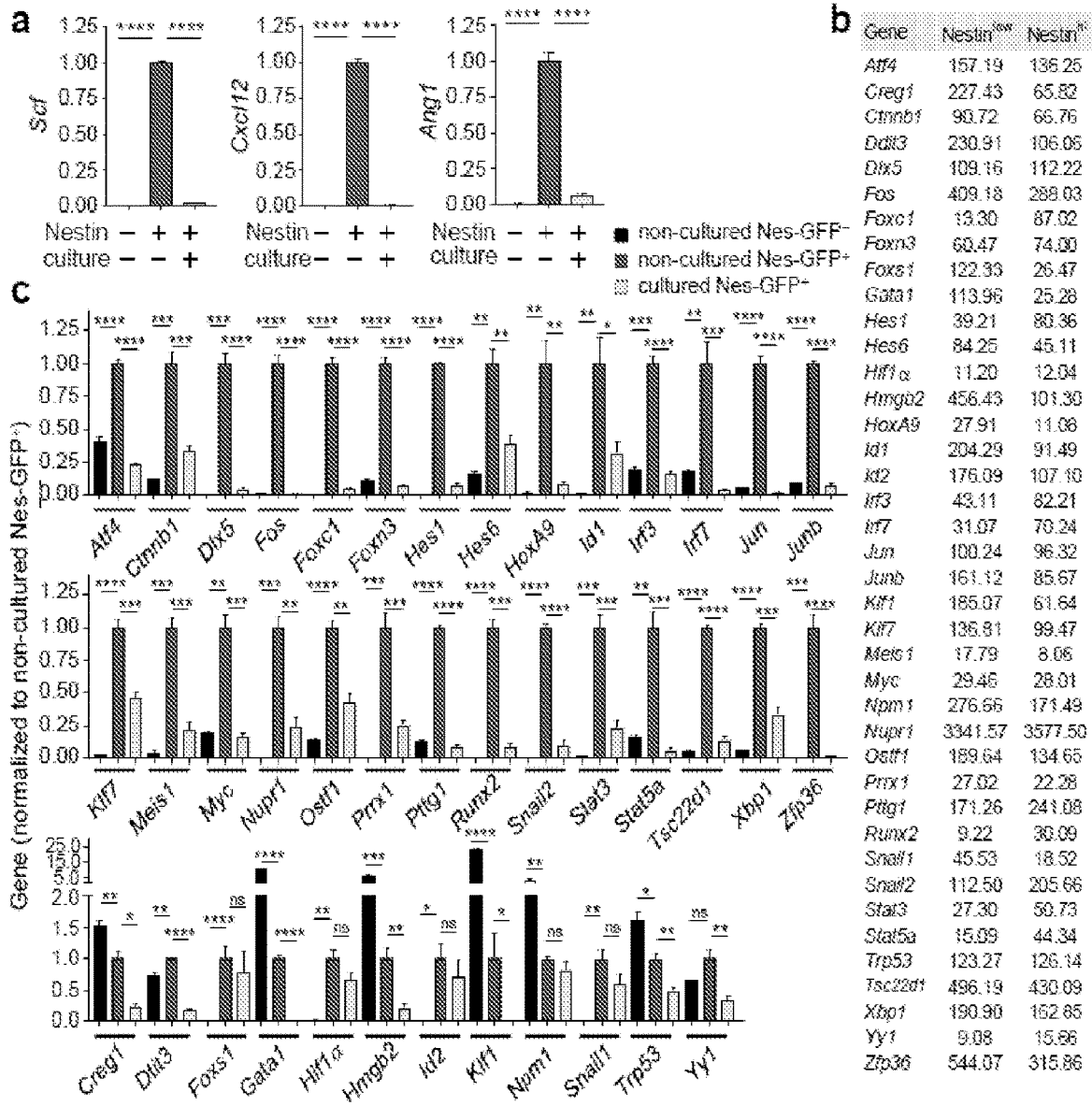
FIG. 1A-1D: Gene expression analysis of HSC niche factors in freshly isolated and cultured Nestin$^+$ MSCs; Selection and screening strategy of candidate revitalizing factors. (a) Quantitative PCR (qPCR) analysis of the expression of Scf, Cxcl12 and Ang1 in freshly isolated stromal (CD45$^-$ Ter119$^+$ CD31$^-$) Nestin-GFP$^-$ and Nestin-GFP$^+$ cells and 2 weeks in vitro cultured Nestin-GFP$^+$ cells isolated from Nes-Gfp transgenic mice. Expression level was normalized with Gapdh level and mean of expression levels in freshly isolated Nestin-GFP$^+$ was defined as 1. (b) Selected 40 candidate genes tested for revitalizing cultured MSCs were derived from RNA-seq analyses of stromal (CD45$^-$ Ter119$^-$ CD31$^-$) Nestin-GFP$^{hi}$ and Nestin-GFP$^{low}$ cells (Kunisaki et. al. Nature 2013). Levels of expression (FPKM) are shown. (c) Quantitative PCR (qPCR) analysis of the expression of 40 candidate genes in freshly isolated Nestin-GFP$^-$ and Nestin-GFP$^+$ MSCs and 2 weeks in vitro cultured Nestin-GFP$^+$ MSCs isolated from Nes-Gfp transgenic mice. 28 genes demonstrating high in freshly isolated Nestin$^+$ MSCs and, low in both freshly isolated Nestin$^+$ MSCs and cultured Nestin$^+$ MSCs (upper panel and middle panel) were selected for the next step of overexpression experiments. Expression level was normalized with Gapdh level and mean of expression levels in freshly isolated Nestin-GFP+ was defined as 1. (d) Scheme of reprogramming platform of cultured MSCs into revitalized MSCs. Isolated MSCs from the bone marrow of Scf-Gfp mice were cultured for 21 days and transduced with a mix of lentivirus harboring 28 genes and grown in adherent culture with alpha-MEM media. On day 7 post transduction, emerged Scf-GFP$^{hi}$ cells were sorted and limiting dilution was performed to isolate single cell derived clones. Identification of virally integrated genes was screened by PCR using specific primers to discriminate from endogenous genes. Error bars, mean±s.e.m. *P<0.05, P<0.01, *P<0.001, ****P<0.0001; Unpaired student's t test (a and c).

An isolated population of artificially modified mesenchymal stem cells (MSC) maintained in culture comprising MSC transduced with one or more vector(s), the vector(s) encoding the following genes: Klf7, Ostf1, Xbp1, Irf3, and Irf7 under conditions permitting expression of the genes.

A method is provided for revitalizing a mesenchymal stem cell (MSC) maintained in culture comprising transducing the MSC with one or more vector(s), the vector(s) encoding the following genes: Ostf1, Xbp1, Irf3, and Irf7 under conditions permitting expression of the genes, so as to revitalize the MSC.

In an embodiment, the vector(s) is/are a lentiviral vector.

In an embodiment, a MSC maintained in culture is revitalized when expression of niche factors Scf, Cxcl12, Vcam1, and/or Ang1 are elicited in the MSC higher than there levels in the MSC in the culture prior to the revitalizing treatment. In an embodiment, expression of niche factors Scf Cxcl12, Vcam1, and Ang1 is elicited.

In an embodiment, the vector(s) further encode the gene Klf7.

In an embodiment, each gene is encoded by a different lentiviral vector. In an embodiment, two or more of the genes are encoded by a single lentiviral vector. In an embodiment, Ostf1, Xbp1, Irf3, and Irf7 are all encoded by a single lentiviral vector. In an embodiment, Klf7, Ostf1, Xbp1, Irf3, and Irf7 are all encoded by a single lentiviral vector.

In an embodiment, Klf7 is the sequence known in the art as NCBI Reference Sequence: NG_052989.1. In an embodiment, Ostf1 encodes the mRNA sequence known in the art as NCBI Reference Sequence: NM_012383.4. In an embodiment, Xbp1 is the sequence known in the art as NCBI Reference Sequence: NC_000022.11. In an embodiment, Irf3 is the sequence known in the art as NCBI Reference Sequence: NC_000019.10. In an embodiment, Irf7 is the sequence known in the art as NCBI Reference Sequence: NC_000011.10.

A method is provided for revitalizing a mesenchymal stem cell (MSC) maintained in culture comprising treating the MSC so as to increase expression of Scf, Cxcl12,Vcam1, and/or Ang1 in the cell, so as to revitalize the MSC.

In an embodiment, the methods further comprise co-culturing a hematopoietic stem cell (HSC) with the revitalized MSC and subsequently harvesting or isolating hematopoietic stem cells from the co-culture. In an embodiment, the MSC is bone-marrow derived. In an embodiment, the HSC is bone-marrow derived or cord blood derived. In an embodiment, the HSC and MSC are obtained from the same individual subject. In an embodiment, the MSC is a human MSC. In an embodiment, the HSC is a human HSC.

Also provided is a kit comprising
  one or more lentiviral vector(s), the lentiviral vector(s) encoding the following genes: Klf7 Ostf1, Xbp1, Irf3, and Irf7;
  one or more reagents for culturing MSCs in vitro; and
  instructions for using the lentiviral vector(s) to revitalize cultured MSCs.

Also provided is a method for expanding hematopoietic stem cells (HSC) comprising providing a culture of mesenchymal stem cells (MSC) pretreated with one or more vector(s), the vector(s) encoding the following genes: Ostf1, Xbp1, Irf3, and Irf7 under conditions permitting expression of the genes, and adding an amount of HSC to the MSC in culture, so as to expand the HSC. In an embodiment, the method further comprises pretreating the MSC with the one or more vector(s). In an embodiment, the vector is/are lentiviral vector(s).

Also provided is a method for co-culturing hematopoietic stem cells (HSC) and mesenchymal stem cells (MSC) comprising providing a culture of MSC pretreated with one or more vector(s), the vector(s) encoding the following genes: Ostf1, Xbp1, Irf3, and Irf7 under conditions permitting expression of the genes, and subsequently adding an amount of HSC to the MSC in culture, so as to co-culture the HSC and MSC. In an embodiment, the vector is/are lentiviral vector(s). In an embodiment, the method further comprises pretreating the MSC with the one or more lentiviral vector(s).

Also provided is a method of transplanting into a subject an amount of hematopoietic stem cells (HSC) previously maintained in co-culture with MSC transduced with one or more vector(s), the vector(s) encoding the following genes: Klf7, Ostf1, Xbp1, Irf3, and Irf7 under conditions permitting expression of the genes. In an embodiment, the HSC previously maintained in culture with MSC have been subjected to artificial gene editing. In an embodiment, the HSC have been separated from the MSC after co-culture with the MSC but prior to transplantation. In an embodiment, the HSC have been separated mechanically from the MSC after co-culture with the MSC but prior to transplantation. For example, mesh separation of the co-culture on top of the MSCs, followed by a light digestion to mechanically dissociate cells from surfaces. In an embodiment, the HSC have been obtained from the subject prior to their co-culture with the MSC.

Also provided is a method of preparing a patient for a bone marrow transplant, comprising administering to the patient an amount of hematopoietic stem cells (HSC) previously maintained in culture with MSC transduced with one or more vector(s), the vector(s) encoding the following genes: Klf7, Ostf1, Xbp1, Irf3, and Irf7 under conditions permitting expression of the genes, the amount of HSC effective to prepare a patient for a bone marrow transplant.

Also provided is a method of preparing a patient for a bone marrow transplant, comprising administering to the patient an amount of mesenchymal stem cells (MSC) previously maintained in culture and which have been transduced with one or more vector(s), the vector(s) encoding the following genes: Klf7, Ostf1, Xbp1, Irf3, and Irf7 under conditions permitting expression of the genes in an amount effective to prepare a patient for a bone marrow transplant.

In an embodiment, the administering to the patient of an amount of the MSC accelerates engraftment of the bone marrow transplant.

In an embodiment of the methods, the vector(s) further encodes the gene Klf7.

In an embodiment, each gene is encoded by a different vector. In an embodiment, two or more of the genes are encoded by a single vector.

In an embodiment of the methods, the vector(s) is/are lentiviral vector(s).

In an embodiment, Ostf1, Xbp1, Irf3, and Irf7 are all encoded by a single lentiviral vector. In an embodiment, Klf7, Ostf1, Xbp1, Irf3, and Irf7 are all encoded by a single lentiviral vector.

Also provided is a method for expanding hematopoietic stem cells (HSC) comprising providing a culture of HSC and mesenchymal stem cells (MSC) pretreated so as to increase expression of Scf, Cxcl12, Vcam1, and/or Ang1 in the MSC, and adding an amount of HSC to the MSC in culture, so as to expand the HSC. In an embodiment, the method further comprises pretreating the MSC with the one or more vector(s). In an embodiment, the vector is/are lentiviral vector(s).

Also provided is a method for co-culturing hematopoietic stem cells (HSC) and mesenchymal stem cells (MSC) comprising providing a culture of MSC pretreated so as to increase expression of Scf, Cxcl12, Vcam1, and/or Ang1 in the MSC and subsequently adding an amount of HSC to the MSC in culture, so as to co-culture the HSC and MSC. In an embodiment, the vector is/are lentiviral vector(s). In an embodiment, the method further comprises pretreating the MSC with the one or more lentiviral vector(s).

Also provided is a method of transplanting into a subject an amount of hematopoietic stem cells (HSC) previously maintained in co-culture with MSC pretreated so as to increase expression of Scf, Cxcl12, Vcam1, and/or Ang1 in the MSC. In an embodiment, the HSC previously maintained in culture with MSC have been subjected to artificial gene editing. In an embodiment, the HSC have been separated from the MSC after co-culture with the MSC but prior to transplantation. In an embodiment, the HSC have been obtained from the subject prior to their co-culture with the MSC.

Also provided is a method of preparing a patient for a bone marrow transplant, comprising administering to the patient an amount of hematopoietic stem cells (HSC) previously maintained in culture with mesenchymal stem cells (MSC) pretreated so as to increase expression of Scf, Cxcl12, Vcam1, and/or Ang1 in the MSC, the amount of HSC effective to prepare a patient for a bone marrow transplant.

Also provided is a method of preparing a patient for a bone marrow transplant, comprising administering to the patient an amount of mesenchymal stem cells (MSC) pretreated so as to increase expression of Scf Cxcl12, Vcam1, and/or Ang1 in the MSC in an amount effective to prepare a patient for a bone marrow transplant.

A method for maintaining a leukemic stem cell (LSC) in culture comprising co-culturing the LSC with MSC transduced with one or more vector(s), the vector(s) encoding the following genes: Ostf1, Xbp1, Irf3, and Irf7 under conditions permitting expression of the genes, so as to revitalize the MSC.

In an embodiment, the vector(s) further encode the gene Klf7. In an embodiment, the vector(s) is/are a lentiviral vector. In an embodiment, each gene is encoded by a different lentiviral vector. In an embodiment, two or more of the genes are encoded by a single lentiviral vector. In an embodiment, Ostf1, Xbp1, Irf3, and Irf7 are all encoded by a single lentiviral vector. In an embodiment, Klf7, Ostf1, Xbp1, Irf3, and Irf7 are all encoded by a single lentiviral vector. In an embodiment, the LSC is a human LSC.

An isolated population of leukemic stem cells (LSC) maintained in culture with MSC transduced with one or more vector(s), the vector(s) encoding the following genes: Klf7, Ostf1, Xbp1, Irf3, and Irf7 under conditions permitting expression of the genes. In an embodiment, the vector(s) is/are lentiviral vector(s).

As used herein, the term "vector" refers to a nucleic acid molecule capable of transporting another nucleic acid to which it has been linked. Preferred vectors are those capable of autonomous replication and/or expression of nucleic acids to which they are linked. The invention is intended to include all forms of expression vectors that serve this functions. In an embodiment the vectors of the invention are lentiviral vectors, but any appropriate vector may be used.

As used herein, the term "expression," with regard to a nucleic acid, refers to the process by which a nucleotide sequence undergoes successful transcription and, for polypeptides, translation such that detectable levels of the delivered nucleotide sequence are expressed. This invention will be better understood from the Experimental Results, which follow. However, one skilled in the art will readily appreciate that the specific methods and results discussed are merely illustrative of the invention as described more fully in the claims that follow thereafter.

EXPERIMENTAL RESULTS

Figure 1D:
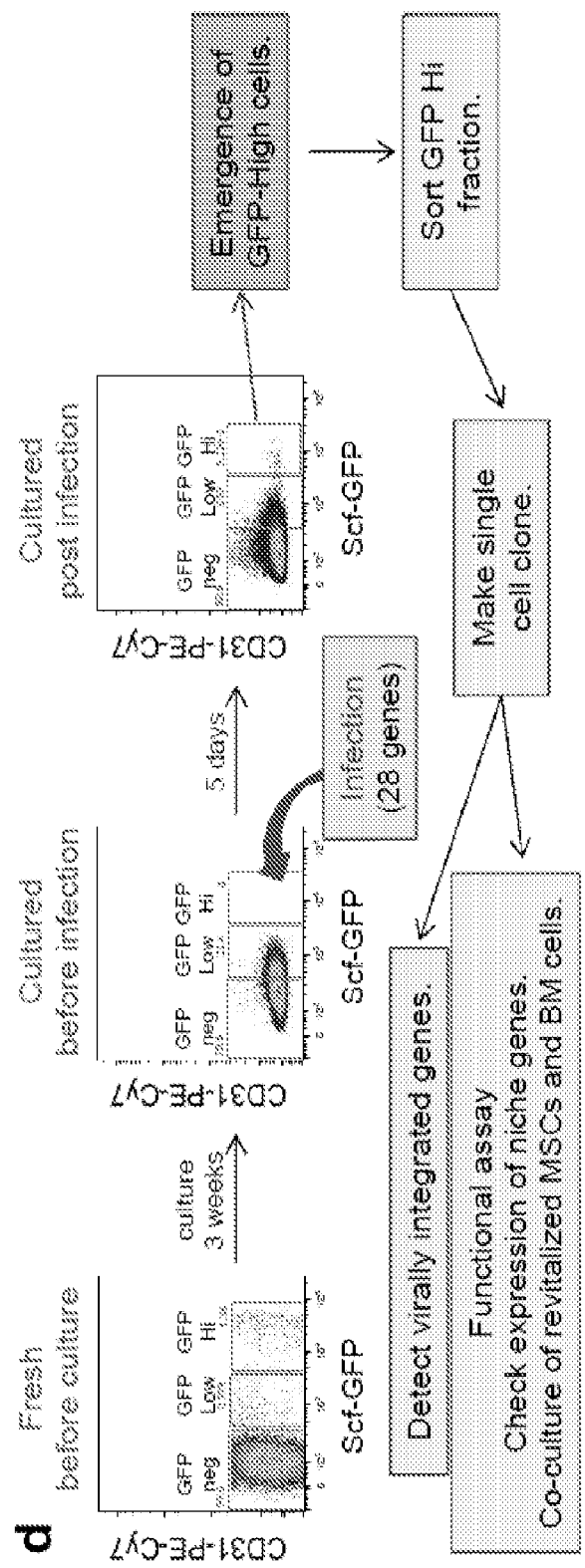

Revitalizing cultured MSCs to boost their synthesis of niche factors and their ability to maintain healthy HSCs in in vitro conditions:

Whole-genome transcriptome RNA sequencing (RNA-seq) analyses of populations of Nestin$^+$ niche MSCs from the bone marrow of mice identified 40 candidate genes, highly expressed by MSCs (FIG. 1b). Next, the list of candidates was narrowed down to 28 (FIG. 2a) by choosing genes which were highly expressed in freshly sorted Nestin⁺ but not in Nestin⁻ MSCs or cultured Nestin⁺ MSCs (FIG. 1c). Lentiviral vectors were then made expressing 28 selected genes. Stem cell factor (Scf)-Gfp knock-in mice-derived cultured bone marrow MSCs which lost the GFP$^{hi}$ fraction after culture were transduced with a mixture of these lentiviral vectors, and re-emerged GFP$^{hi}$ cells after transduction were sorted to screen for a combination that would revitalize cultured MSCs prompting these cells to regain their expression of niche factors such as Scf and also reacquire lost in vivo MSC niche functions (FIG. 1d).

Figures 2A, 2B:
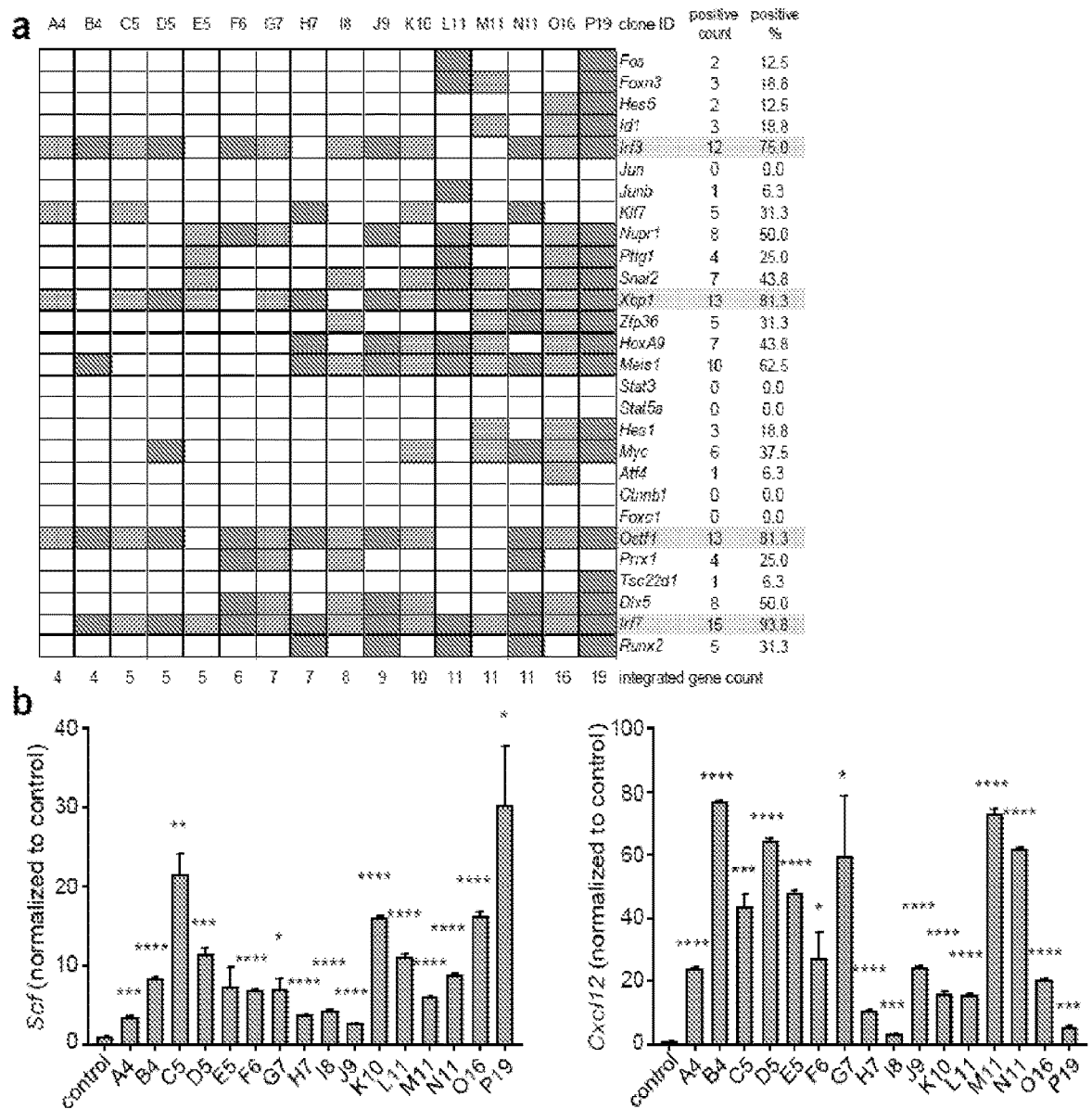
FIG. 2A-2F: Klf7, Ostf1, Xbp1, Irf3, and Irf7 reprogram cultured MSCs into revitalized MSCs able to maintain and expand HSCs in in vitro conditions. (a) Summary of data showing presence (blue or orange) or absence (white) of each of the indicated factors in each revitalized MSC clone derived from Scf-GFP$^{hi}$ MSCs transduced with a mix of lentivirus harboring 28 genes. Count of factors positive in each clone is shown in right column. Genes whose positive rate of integration is more than 75% are highlighted in yellow. Number in the name of each clone indicates integrated gene count. (b) The expression of bone marrow niche genes (Scf and Cxcl12) was assessed in each clone by quantitative PCR (qPCR) analysis. Statistics was performed comparing with the expression in empty vector transduced control MSCs. Expression level was normalized with βActin level and mean of expression levels in empty vector transduced control MSC was defined as 1. (c) Lineage negative bone marrow cells were co-cultured with each clone of revitalized MSCs in the presence of 20 ng/ml SCF and 10 ng/ml TPO. After 6 days, HSC (LSK CD150+ CD48−) and LSK (Lineage− c-Kit+ Scal+) cell numbers was assessed by FACS analysis. Statistics was performed comparing with the cell count in co-culture with empty vector transduced control MSCs. (d) Expression of Scf was assessed by qPCR in empty vector transduced control MSC, 4 genes (Ostf1, Xbp1, Irf3, and Irf7) transduced MSC clone (OXII), and 5 genes (Klf7, Ostf1, Xbp1, Irf3, and Irf7) transduced MSC clone (KOXII). Expression level was normalized with βActin level and mean of expression levels in empty vector transduced control MSC was defined as 1. (e) Lineage negative bone marrow cells were co-cultured with empty vector transduced control MSC clone, 4 genes (Ostf1, Xbp1, Irf3, and Irf7) transduced MSC clone (OXII), and 5 genes (Klf7, Ostf1, Xbp1,Irf3, and Irf7) transduced MSC clone (KOXII) in the presence of 20 ng/ml SCF and 10 ng/ml TPO. After 6 days, HSC (LSK CD150+ CD48−) and LSK (Lineage− c-Kit+ Scal+) cell numbers was assessed by FACS analysis. (0 Phase-contrast images of MSC clone transduced with empty vector (control) and MSC clone transduced with 5 genes (Klf7, Ostf1, Xbp1, Irf3, and Irf7) (KOXII). (scale bar represents 50 pin) Error bars, mean±s.e.m. in (b and d), mean±s.d. in (c and e). *P<0.05, P<0.01, *P<0.001, ****P<0.0001; Unpaired student's t test (b-e).
Figures 2C, 2D, 2E:
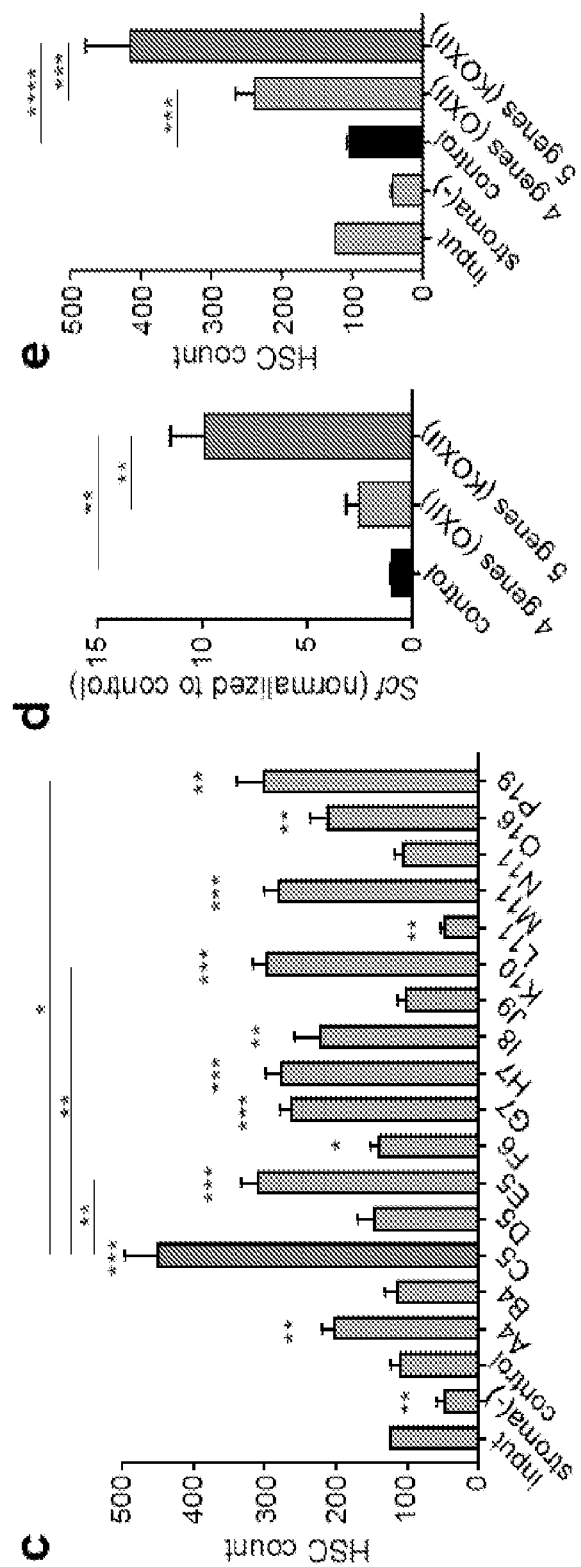
Figure 2F:
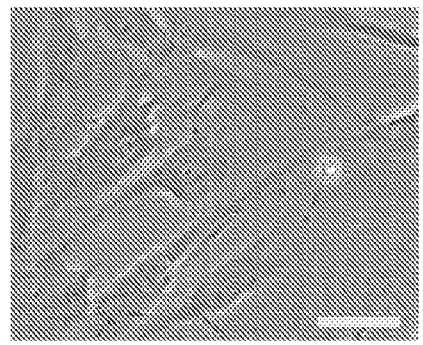
Figure 2F:
Figures 3A, 3B:
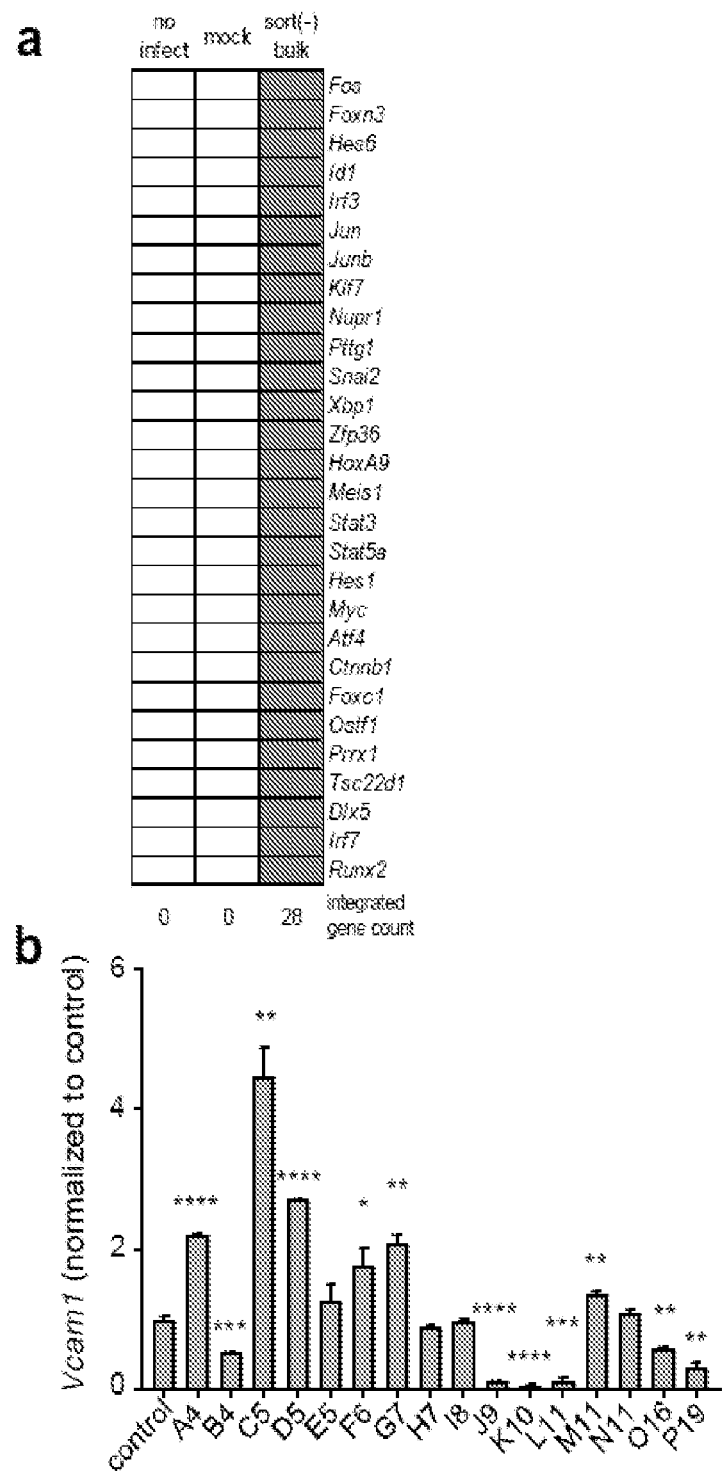
FIG. 3A-3D: Combination of 4 genes (Ostf1, Xbp1, Irf3, and Irf7) or 5 genes (Klf7, Ostf1, Xbp1, Irf3, and Irf7) is required to expand MSC clones after transduction. (a) Data showing presence (gray) or absence (white) of virally integrated genes in cultured MSCs before transduction (no infect), transduced with empty vector (mock), or transduced with mix of lentivirus harboring 28 genes without sorting Scf-GFP$^{hi}$ fraction (sort− bulk). (b) The expression of bone marrow niche genes (Vcam1 and Ang1) was assessed in each clone by quantitative PCR (qPCR) analysis. Statistics was performed comparing with the expression in empty vector transduced control MSCs. Expression level was normalized with βActin level and mean of expression levels in empty vector transduced control MSC was defined as 1. (c) Expression of bone marrow niche genes (Cxcl12, Vcam1 and Ang1) was assessed by qPCR in empty vector transduced control MSC, 4 genes (Ostf1, Xbp1, Irf3, and Irf7) transduced MSC clone (OXII), and 5 genes (Klf7, Ostf1, Xbp1, Irf3, and Irf7) transduced MSC clone (KOXII). Expression level was normalized with βActin level and mean of expression levels in empty vector transduced control MSC was defined as 1. (d) Isolated MSCs from Scf-gfp mice bone marrow were cultured for 21 days and transduced with mix of lentivirus harboring 4 genes (Ostf1, Xbp1, Irf3, and Irf7) or 4 genes minus the indicated factor, or 4 genes plus Klf7 (KOXII). On day 7 post transduction, emerged Scf-GFP$^{hi}$ cells were sorted and cultured for 14 days then cell count was assessed. Error bars, mean±s.e.m. in (b and c), mean±s.d. in (d). *P<0.05, P<0.01, *P<0.001, ****P<0.0001; Unpaired student's t test (b, c, and d).
Figures 3C, 3D:
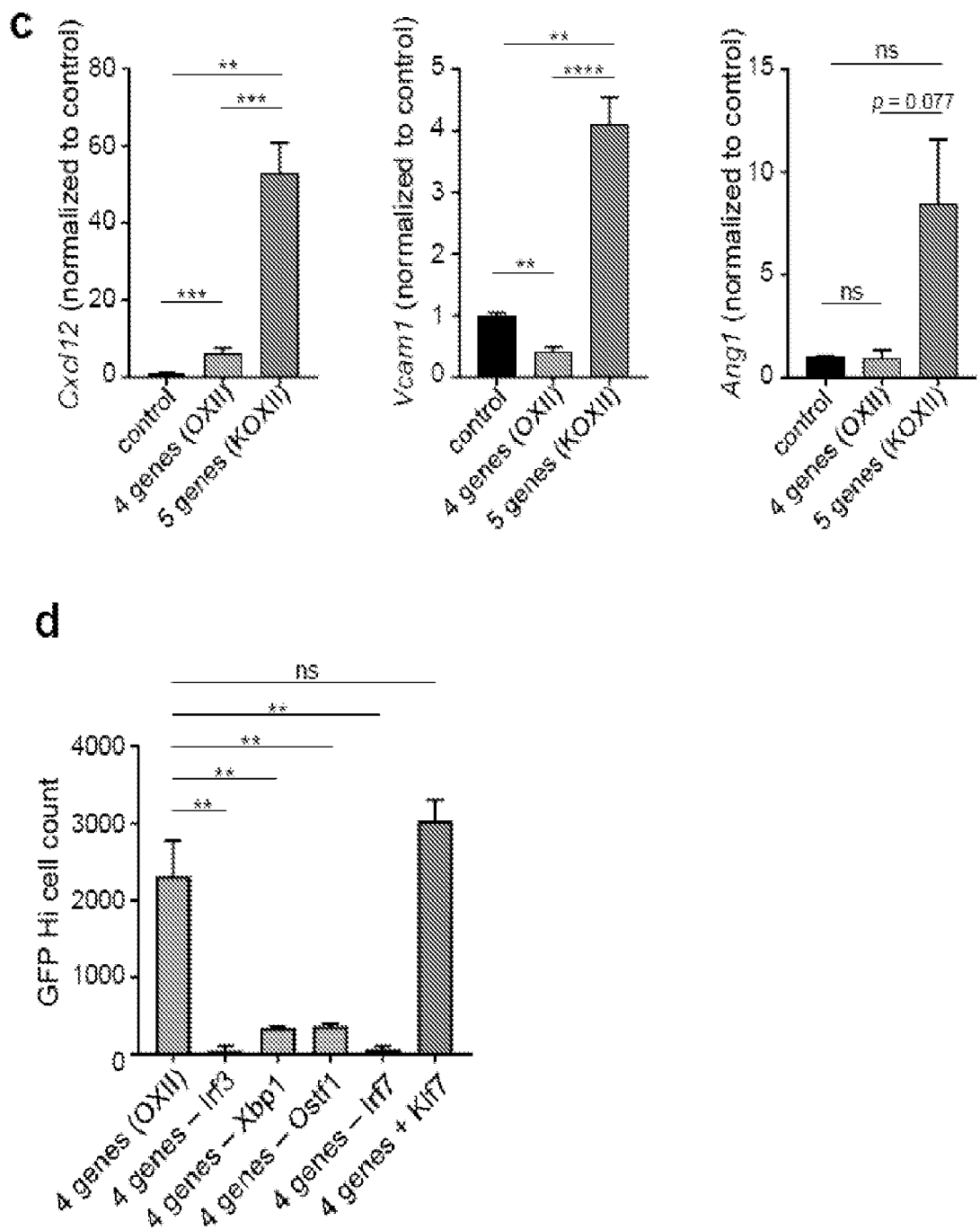
Figure 4A:
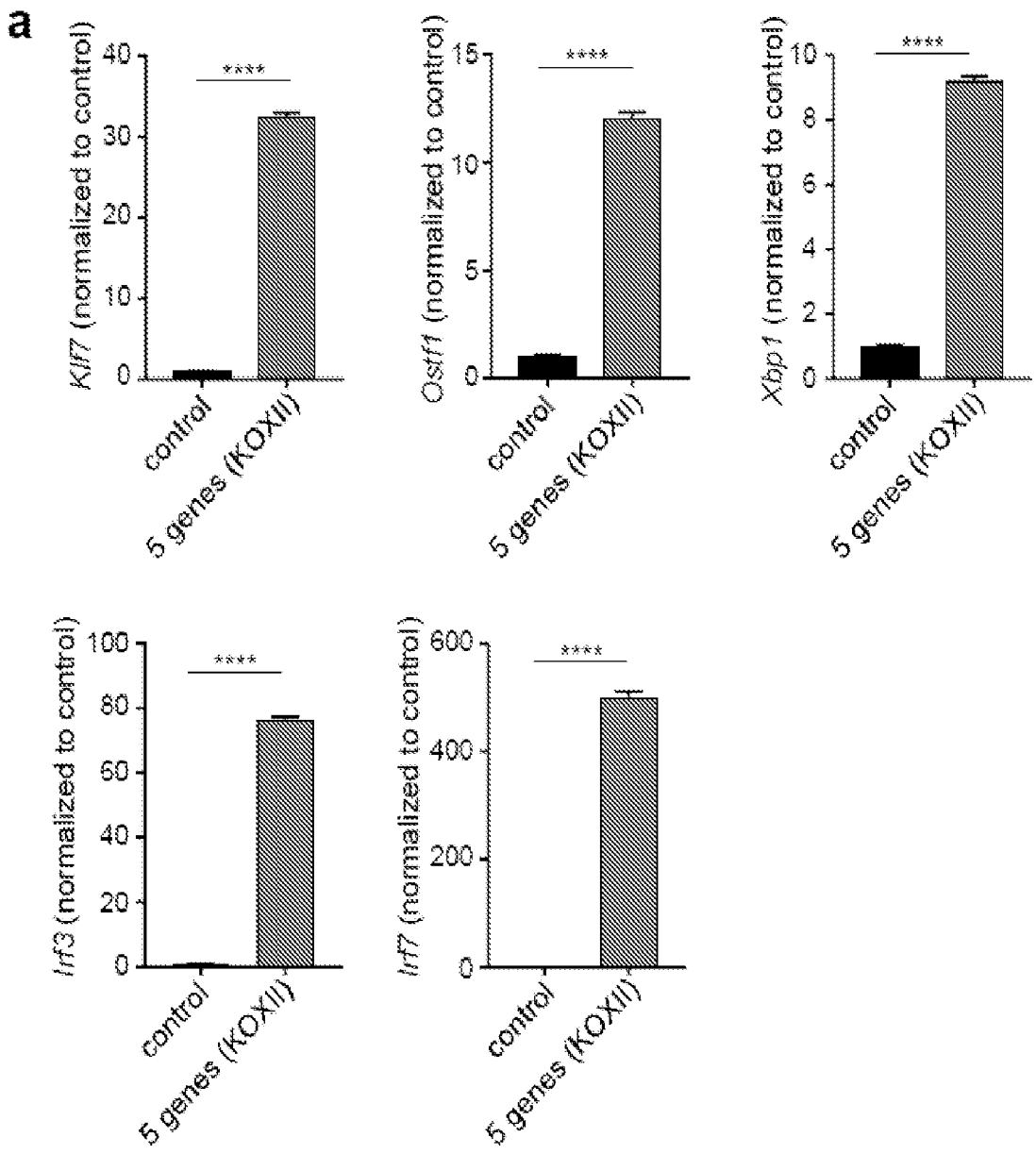
FIG. 4A: The expression of the 5 virally integrated factors was high in the transduced MSC clone KOXII. (a) The expression of the indicated virally integrated factors (Klf7, Ostf1, Xbp1, Irf3, and Irf7) was assessed by quantitative PCR (qPCR) analysis in empty vector transduced MSCs (control) and 5 genes (Klf7, Ostf1, Xbp1, Irf3, and Irf7) transduced revitalized MSCs (KOXII). Expression level was normalized with βActin level and mean of expression levels in empty vector transduced control MSC was defined as 1. Error bars, mean±s.e.m. in (a). *P<0.05, P<0.01, *P<0.001, ****P<0.0001; Unpaired student's t test (a).
Figures 5A, 5B, 5C, 5D:
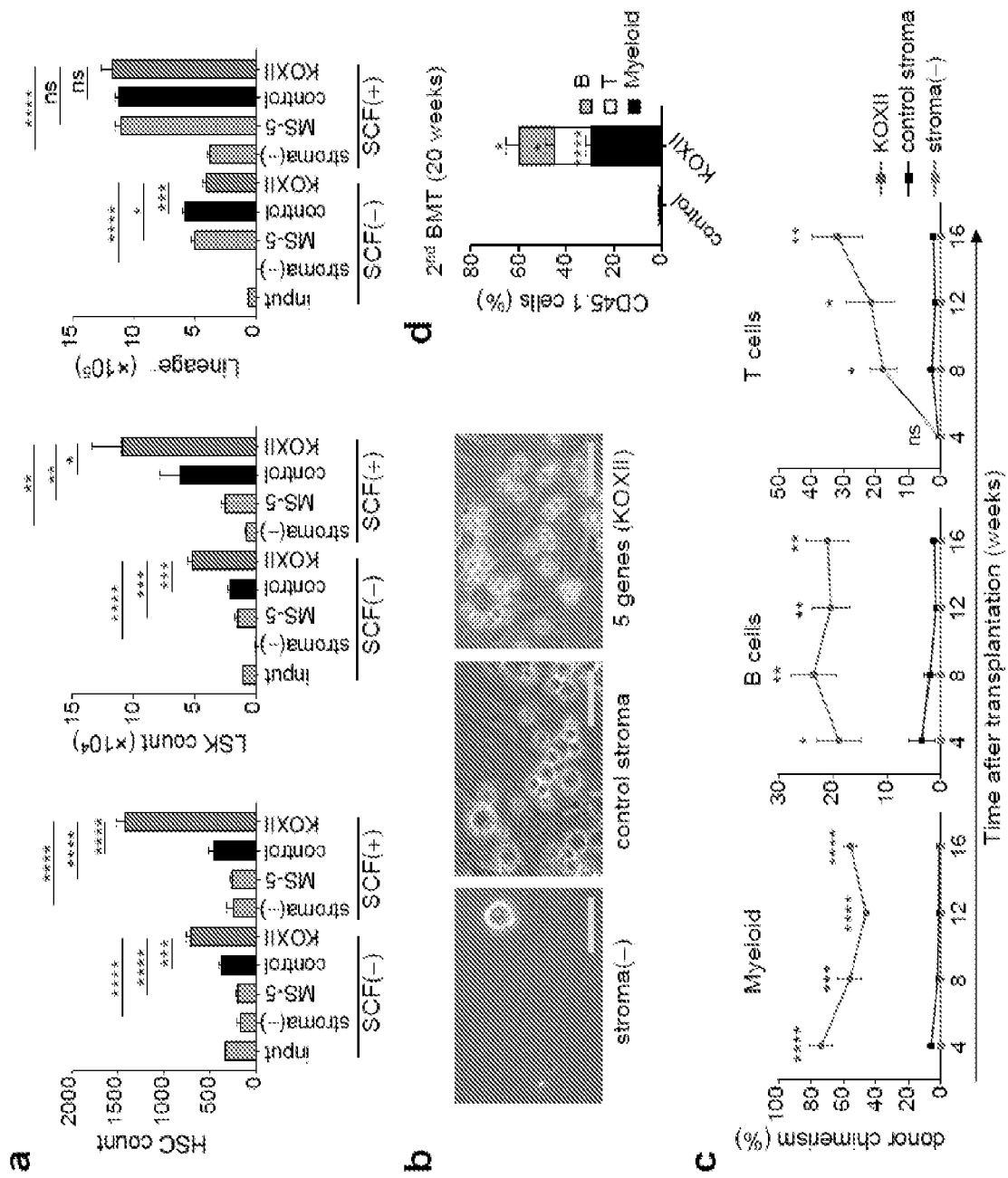
FIG. 5A-5E: HSCs expanded in co-culture with revitalized MSCs show higher engraftment compared to control MSCs after bone marrow transplantation. (a) Lineage negative bone marrow cells were co-cultured with the MS-5 stromal cell line, empty vector transduced MSC (control), 5 genes (Klf7, Ostf1, Xbp1, Irf3, and Irf7) transduced revitalized MSC (KOXII), or without stromal cells with 10 ng/ml TPO in the presence or absence of 20 ng/ml SCF. Quantification of HSC (LSK CD150+ CD48), LSK (Lin− Scal+ cKit+) and Lineage− cell numbers assessed 6 days post co-culture. (b) Phase-contrast images of lineage negative bone marrow cells co-cultured with empty vector transduced MSCs (control), 5 genes (Klf7, Ostf1, Xbp1, Irf3, and Irf7) transduced revitalized MSCs (KOXII), or without stromal cells. (c) Quantification of tri-lineage (myeloid, B cell and T cell) engraftment by FACS in the blood of mice transplanted with lineage negative bone marrow cells co-cultured with control MSCs, 5 genes transduced revitalized KOXII MSCs, or without stromal cells, by competitive reconstitution assay. Statistics was performed comparing to donor chimerism in control. (d) Quantification of long-term tri-lineage engraftment from the primary transplantation shown in (c), in a secondary competitive reconstitution assay. (e) Survival curve of recipient mice given lethal radiation and transplanted with freshly isolated 40,000 or 25,000 bone marrow mononuclear cells (BMMNCs) from C57BL/6 mice, or transplanted with whole cultured CD45+ cells derived from co-culture of 40,000 or 25,000 C57BL/6 BMMNCs with control MSCs, 5 genes transduced revitalized KOXII MSCs, or without stromal cells, by non-competitive assay. Bars: (b) 50 μm. Error bars, mean±s.d. in (a, c and d). *P<0.05, P<0.01, *P<0.001, ****P<0.0001; Unpaired student's t test (a, c and d). Log-rank analysis was used for the Kaplan-Meier survival curves in (e).
Figure 5E:
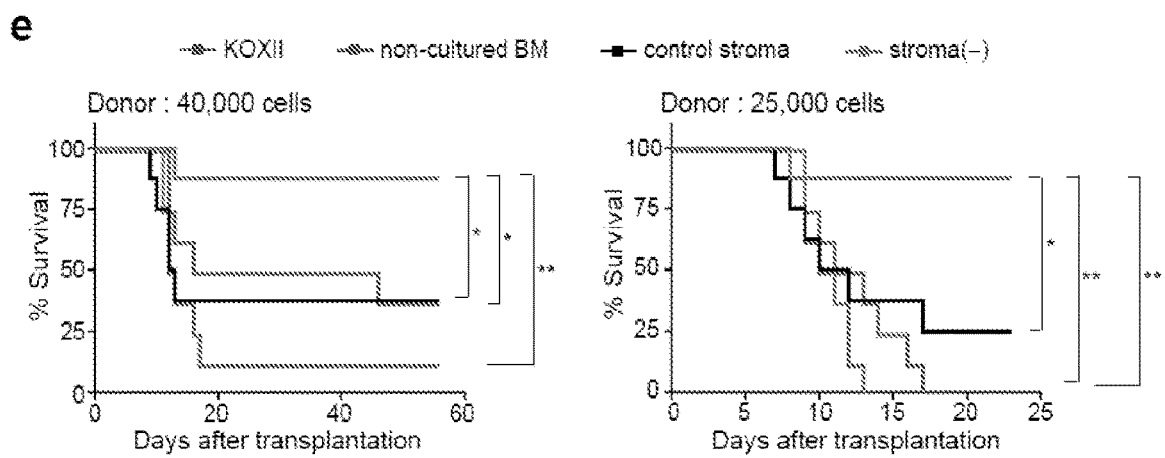

After generating 16 different single cell clones, a combination of 5 genes (Klf7, Ostf1, Xbp1, Irf3, and Irf7) was identified that can reproducibly revitalize cultured MSCs inducing expression of niche factors Scf, Cxcl12, Vcam1, and Ang1 (FIG. 2b and FIG. 3b). These revitalized MSCs are able to maintain and expand HSCs in vitro with very little exogenous help from external hematopoietic cytokines; expanding phenotypic HSCs to more than 2.1-fold without stem cell factor (SCF), and to more than 4.2-fold with SCF (FIG. 5a). Furthermore, it is shown that functional HSC numbers expand in co-culture with revitalized MSCs as much higher engraftment after bone marrow transplantation is observed, compared to empty vector-transduced control MSCs (FIG. 5c) and this advantage was dramatic upon secondary transplantation (FIG. 5d). In addition, the ability to radio-protect lethally irradiated animals was significantly improved, particularly in the setting of low BM cells (25,000) transplantation (FIG. 5e), which is promising in the context of cord blood-derived stem cell expansion.

Figures 7A, 7B:
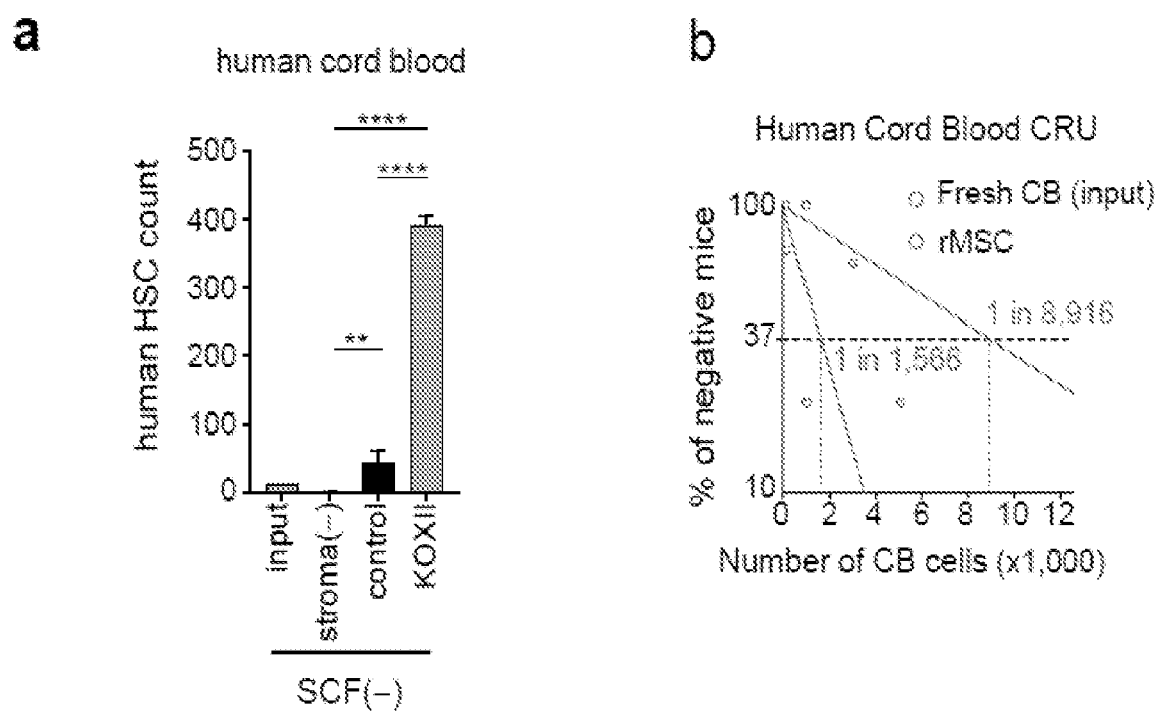
FIG. 7A-7B: (a) Human HSCs expanded in co-culture with revitalized murine MSCs. Human cord blood cells were co-cultured with the empty vector transduced murine MSC (control), 5 genes (Klf7, Ostf1, Xbp1, Irf3, and Irf7) transduced revitalized murine MSC (KOXII), or without stromal cells with 10 ng/ml human TPO in the absence of SCF. Quantification of human HSC (Lin−CD34−CD38+CD90+CD49f+) numbers assessed 6 days post co-culture. (b) CRU assay using limiting numbers of CD34+ cells from human cord blood, or human cord blood CD34+ cells co-cultured with murine rMSCs. Freshly isolated CD34+ cells from human cord blood were immediately used for BM transplantation into NOD-scid Il2rg−/− (NSG) immunocompromised mice, or co-cultured with rMSCs for 6 days, and then a fraction of the cultured cells corresponding to the indicated number (0.2, 1, 3 and $5 \times 10^3$) of initial cord blood cells was transplanted into NSG mice. Percent chimerism of donor cells in the recipient peripheral blood was determined at 16 weeks after transplantation. Mice with donor chimerism >1% were considered successfully engrafted and the others were scored as negative. n=5 mice for each group. Error bars, mean±s.d. *$P<0.05$, $P<0.01$, *$P<0.001$, ****$P<0.0001$; Unpaired student's t test. Log-rank analysis was used for the Kaplan-Meier survival curves in (b).

In addition, further testing showed that these revitalized murine MSCs are able to maintain and expand human HSCs in vitro; expanding phenotypic human cord blood-derived HSCs to more than 28-fold without SCF (FIG. 7A). Competitive transplantation assays were also carried out using limiting dilutions of fresh and CD34+ cells from human cord blood expanded for 6 days with murine rMSC in serum-free media supplemented with human SCF and human TPO. The frequency of long-term repopulating HSCs was increased ~6-fold (from 1 in 8,916 fresh CB cells to 1 in 1,566 in rMSC-expanded cells; FIG. 7b). These data demonstrate that murine rMSCs are capable of efficiently expanding functional human HSCs.

To evaluate the extent of which rMSCs resemble freshly isolated MSCs, we employed RNA-seq analysis to compare the transcriptome of freshly sorted CD45− Ter119− CD31− Scf-GFP− cells, CD45− Ter119− CD31− Scf-GFP+ cells, rMSCs and control vector-transduced stroma. HSC niche-associated genes were highly expressed in both native Scf-GFP+ stromal cells and rMSCs compared to the Scf-GFP− cell fraction and cultured control MSCs. Interestingly, several niche-associated genes (e.g. Runx2, Sp7, Bmp5 and Ptn) that are also known regulators of osteogenesis were not fully restored in rMSCs compared to native Scf-GFP+ stromal cells, likely explaining the reduced in vitro osteogenic differentiation capacity of rMSCs. Principal component analysis (PCA) revealed that the 4 populations clustered independently. Next assessed was the overlap of upregulated genes in rMSCs compared to cultured control MSCs and genes upregulated in freshly isolated native Scf-GFP+ stromal cells compared to native Scf-GFP− cells. It was found that 235 genes overlapped between these two groups, and pathway analysis revealed a highly significant increase in Rap1 signalling and Axon guidance pathways, and PI3K-Akt and Ras signalling which are important for cell survival and proliferation (FIG. 8d). Interestingly, the enrichment analysis also showed significant upregulation of TGF-β signalling which is reported to promote HSC quiescence. These data indicate that although rMSCs are reprogrammed to regain HSC niche function, they remain distinct from their endogenous counterparts.

To investigate the revitalization mechanism induced by the 5 genes (KOXII), we interrogated by Assay for Transposase Accessible Chromatin with high-throughput sequencing (ATAC-seq) the accessible DNA regions in our 4 studied populations. We found that revitalization of MSCs led to 8,997 peaks of open chromatin in rMSCs when compared to control MSCs. Of these, 626 open peaks were also detected in freshly isolated Scf-GFP+ cells when compared to Scf-GFP− cells. Pathway analysis of the common 626 peaks showed overlapping pathways with those identified in RNA-seq analysis.

Figures 6A, 6B, 6C, 6D, 6E:
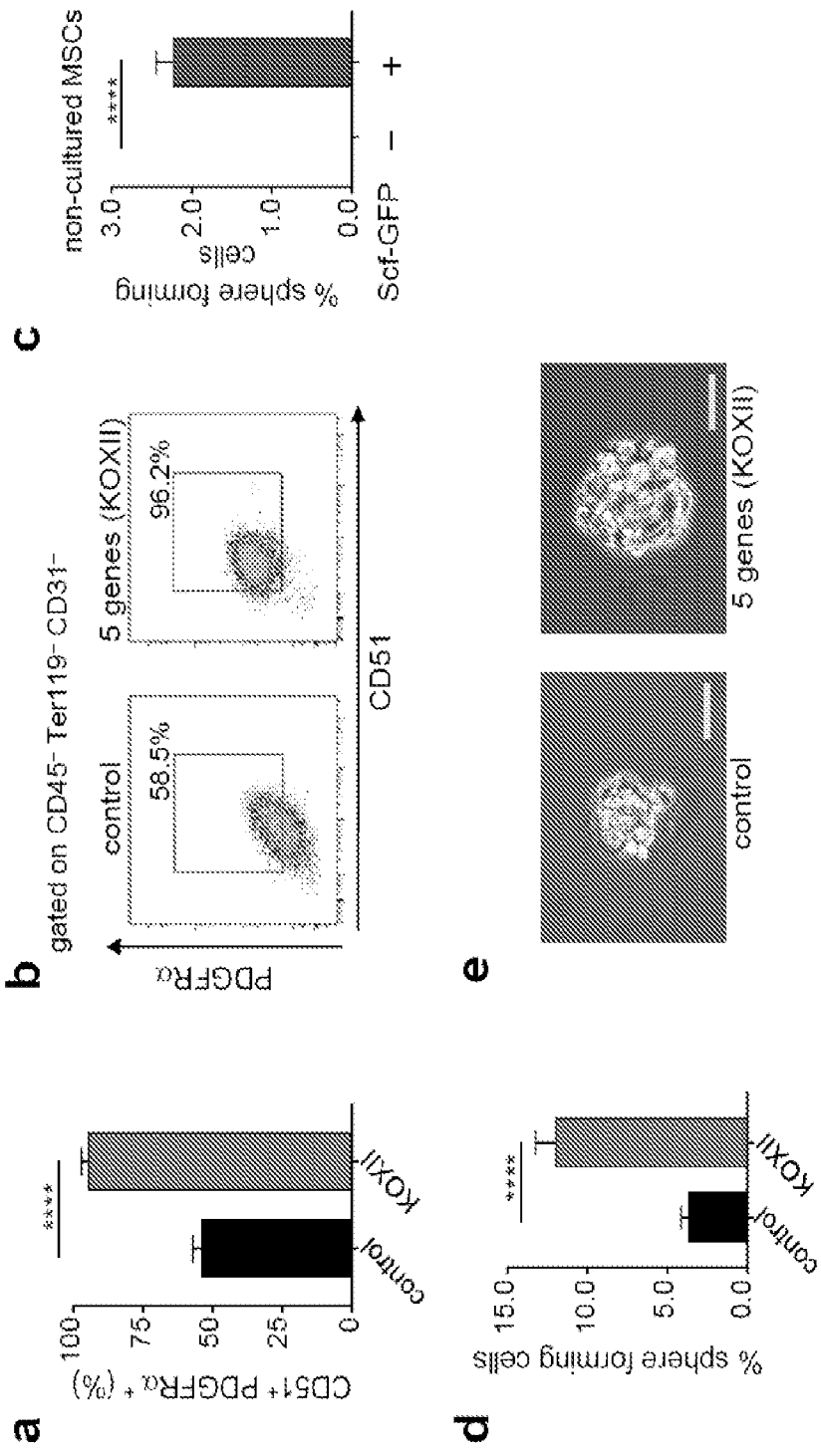
FIG. 6A-6I: Characterization of revitalized KOXII MSCs. (a) PDGFRα+ CD51+ cell frequency in the stromal population of cells transduced with empty vector (control) or transduced with 5 genes (Klf7, Ostf1, Xbp1, Irf3, and Irf7), the revitalized MSCs (KOXII). (b) FACS analysis plot of representative sample from (a). (c) Self-renewing sphere forming capacity was assessed by plating Scf-GFP⁻ or Scf-GFP⁺ MSCs freshly sorted from bone marrow at clonal densities. (d) Self-renewing sphere forming capacity was assessed by plating empty vector transduced MSCs (control) or 5 genes (Klf7, Ostf1, Xbp1, Irf3, and Irf7) transduced revitalized MSCs (KOXII) at clonal densities. (e) Phase-contrast images of self-renewing spheres in (d). (f-h) Multilineage differentiation capacity of control and KOXII MSCs. Fully differentiated phenotypes of control and KOXII MSCs were tested by Oil Red O (adipogenic; f), Alizarin Red S (osteogenic; g), and Alcian Blue (chondrogenic; h) stainings. (i) Differentiation kinetic of empty vector transduced MSCs (control) and 5 genes (Klf7, Ostf1, Xbp1, Irf3, and Irf7) transduced revitalized MSCs (KOXII) was evaluated by real-time PCR for the expression of adipogenic specific gene (Pparg) at days 0, 14 or osteogenic specific gene (Sp7) at days 0, 20. Expression level was normalized with βActin level and mean of expression levels in day 0 control MSC was defined as 1. Bars: (e-g) 50 µm; (h) 1 mm. Error bars, mean±s.d. in (a, c and d), mean±s.e.m. in (i). *$P<0.05$, $P<0.01$, *$P<0.001$, ****$P<0.0001$; Unpaired student's t test (a, c, d and i).
Figures 6F, 6G, 6H, 6I:
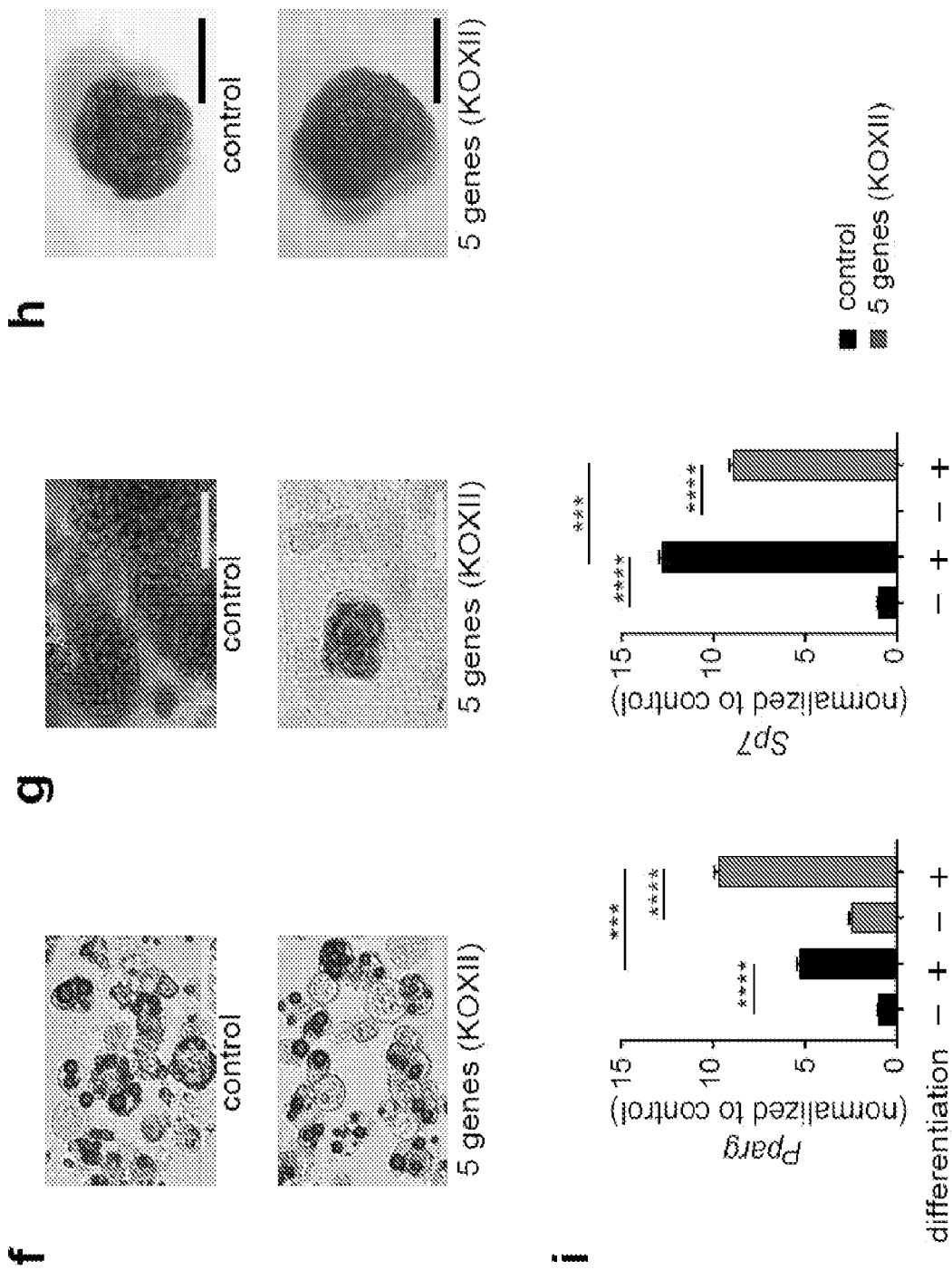

The impact of the 5 gene revitalization (KOXII) on MSC activity has been characterized. KOXII increases expression of the MSC markers PDGFa and CD51 on stromal cells (FIGS. 6a and b) whose sphere-forming ability is confined in the Scf-GFP+ subset (FIG. 6c). KOXII cells have higher sphere-forming frequency and forms bigger spheres (FIGS. 6d and e), suggesting that MSC functions are maintained. KOXII maintained the capacity to differentiate toward the three mesenchymal lineages: fat (FIG. 6f), bone (FIG. 6g) and cartilage (FIG. 6h) but the ability in osteogenic differentiation appears suppressed, a finding confirmed by gene expression analyses. In summary, a new method is provided to maintain and expand human bone marrow or cord blood-derived stem cells which will improve transplantation across HLA barriers.

What is claimed is:

1. A modified mesenchymal stem cell (MSC) comprising a mesenchymal stem cell (MSC) modified to express the genes Ostf1 (osteoclast stimulating factor 1), Xbp1 (X-box binding protein 1), Irf3 (interferon regulatory factor 3), and Irf7 (interferon regulatory factor 7), wherein the MSC is modified by transduction with one or more vector(s) encoding the genes Ostf1, Xbp1, Irf3, and Irf7, and wherein the modified MSC is a revitalized MSC.

2. The composition of claim 1, wherein the MSC is further modified to express the Klf7 (Kruppel-like factor 7) gene.

3. The composition of claim 2, wherein the mesenchymal stem cell (MSC) is modified by transduction to express the Klf7 gene.

* * * * *